(12) United States Patent
Dath et al.

(10) Patent No.: US 8,536,396 B2
(45) Date of Patent: *Sep. 17, 2013

(54) PRODUCTION OF OLEFINS

(75) Inventors: Jean-Pierre Dath, Beloeil (BE); Walter Vermeiren, Houthalen (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 1061 days.

This patent is subject to a terminal disclaimer.

(21) Appl. No.: 10/524,640

(22) PCT Filed: Aug. 13, 2003

(86) PCT No.: PCT/EP03/09141
§ 371 (c)(1),
(2), (4) Date: May 30, 2006

(87) PCT Pub. No.: WO2004/016572
PCT Pub. Date: Feb. 26, 2004

(65) Prior Publication Data
US 2006/0235251 A1 Oct. 19, 2006

(30) Foreign Application Priority Data
Aug. 14, 2002 (EP) .................................... 02078355

(51) Int. Cl.
*C07C 1/20* (2006.01)
(52) U.S. Cl.
USPC ............................ 585/640; 585/638; 585/639
(58) Field of Classification Search
USPC ................. 585/651–653, 639, 640, 500, 638; 208/109, 113, 114, 118, 120.01, 130
See application file for complete search history.

(56) References Cited

U.S. PATENT DOCUMENTS

| 3,709,979 | A | * | 1/1973 | Chu ............................... 423/700 |
| 4,025,575 | A | * | 5/1977 | Chang et al. ................... 585/640 |
| 4,061,724 | A | | 12/1977 | Grose et al. |
| 4,393,265 | A | * | 7/1983 | Bonifaz ......................... 585/639 |
| 4,524,235 | A | | 6/1985 | Banks et al. |
| 4,527,001 | A | | 7/1985 | Kaiser |
| 4,559,314 | A | * | 12/1985 | Shihabi ........................... 502/71 |
| 4,579,993 | A | * | 4/1986 | Bowes et al. .................. 585/640 |
| 4,621,161 | A | * | 11/1986 | Shihabi ........................ 585/408 |
| 4,849,573 | A | * | 7/1989 | Kaeding ........................ 585/640 |
| 4,861,938 | A | | 8/1989 | Lewis et al. |
| 5,063,187 | A | | 11/1991 | Burgfels et al. |

(Continued)

FOREIGN PATENT DOCUMENTS
EP 0 123 449 A1 10/1984
EP 142313 A1 * 5/1985

(Continued)

*Primary Examiner* — In Suk Bullock
*Assistant Examiner* — Bradley Etherton

(57) ABSTRACT

A process for converting a hydrocarbon feedstock to provide an effluent containing light olefins, the process comprising passing a hydrocarbon feedstock, the feedstock containing at least one $C_1$ to $C_6$ aliphatic hetero compound selected from alcohols, ethers, carbonyl compounds and mixtures thereof and steam in an amount whereby the feedstock contains up to 80 weight % steam, through a reactor containing a crystalline silicate catalyst to produce an effluent including propylene, the crystalline silicate having been subjected to de-alumination by a steaming step and being selected from at least one of an MFI-type crystalline silicate having a silicon/aluminium atomic ratio of from 250 to 500 and an MEL-type crystalline silicate having a silicon/aluminium atomic ratio or from 150 to 800.

15 Claims, 1 Drawing Sheet

(56) References Cited

U.S. PATENT DOCUMENTS

Figure 1:
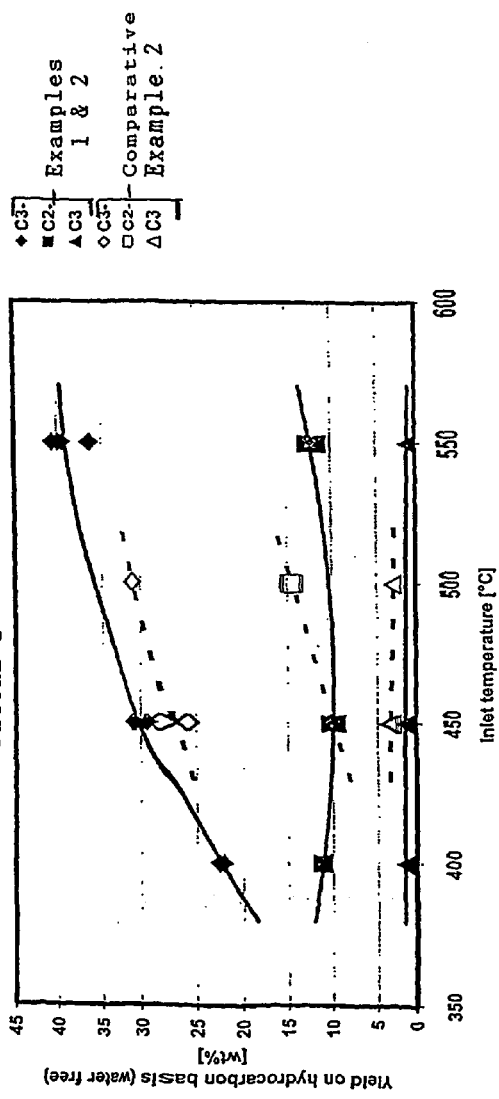

| | | | |
|---|---|---|---|
| 5,095,163 A | 3/1992 | Barger | |
| 5,126,308 A | 6/1992 | Barger et al. | |
| 5,990,369 A * | 11/1999 | Barger et al. | 585/640 |
| 6,033,555 A | 3/2000 | Chen et al. | |
| 6,222,087 B1 * | 4/2001 | Johnson et al. | 585/651 |
| 6,646,175 B1 | 11/2003 | Dath et al. | |
| 6,646,176 B1 | 11/2003 | Dath et al. | |
| 6,713,658 B1 | 3/2004 | Dath et al. | |
| 2003/0062291 A1 * | 4/2003 | Dath et al. | 208/120.01 |
| 2003/0181777 A1 * | 9/2003 | Powers et al. | 585/648 |

FOREIGN PATENT DOCUMENTS

| | | |
|---|---|---|
| EP | 0 448 000 A1 | 9/1991 |
| EP | 0 882 692 A1 | 12/1998 |
| EP | 0 921 181 A1 | 6/1999 |
| WO | WO 99/29802 A1 | 6/1999 |
| WO | WO 99/29805 A1 | 6/1999 |

* cited by examiner

PRODUCTION OF OLEFINS

The present invention relates to a process for converting an oxygen containing hydrocarbon feedstock to produce an effluent containing light olefins, in particular propylene.

There is an increasing demand for light olefins, for example ethylene and propylene, in the petrochemical industry, in particular for the production of polymers, in particular polyethylene and polypropylene. In particular, propylene has become an increasingly valuable product and accordingly there has been a need for the conversion of various hydrocarbon feedstocks to produce propylene.

Increasing amounts of stranded or associated natural gas are being found throughout the world. It becomes important to valorize these gas reserves, not only as fuel but if possible as a carbon source for chemicals and liquid transportable fuel. One way of doing this is the conversion of natural gas into synthesis gas and consequently synthesis of methanol that can serve as a primary source of other chemicals or liquid fuels.

It has been known for a number of years to convert low molecular weight monohydric alcohols such as methanol into light olefins, with the effluent containing ethylene and propylene. Methanol can readily be produced from methane present in natural gas, which is in abundant supply, and is in oversupply in some oil-producing regions of the world. There is therefore a need to produce light olefins such as ethylene and propylene from feedstocks derived from natural gas.

The conversion of a feed containing $C_1$ to $C_4$ monohydric alcohols to olefinic hydrocarbons including ethylene and propylene has been known at least since the 1970's. For example U.S. Pat. No. 4,148,835 in the name of Mobil Oil Corporation discloses a catalytic process for converting a feed containing a $C_1$ -$C_4$ monohydric alcohol, in particular methanol, by contact of the alcohol, under conversion conditions, with a catalyst comprising a crystallised alumina silicate zeolite having a crystallite size at least about 1 micron, a silica to alumina ratio of at least about 12 and a constraint index within the approximate range of 1 to 12. In particular, the zeolite comprises ZSM 5. The effluent from the methanol conversion includes ethylene and propylene. The problem of the process disclosed in U.S. Pat. No. 4,148,835 is that the propylene yield is not very high and there is a need to increase the propylene yield of the conversion process. EP-A-0123449, also in the name of Mobil Oil Corporation, discloses a process for converting alcohols/ethers, especially methanol, into olefins over zeolite catalysts. Olefin selectivity is enhanced by using zeolites of crystal size less than 1 micron and which have been steamed to alpha values of not more than 50, preferably 5 to 35. However, although the mixture of olefins produced contains mostly ethylene, propylene and the butylenes with a small pentenes component, there is no disclosure of a process which has a high propylene selectivity.

DE-A-2935863, and its equivalent U.S. Pat. No. 4,849,753, also in the name of Mobil Oil Corporation, disclose a process for producing light olefins by catalytically converting methanol over crystalline aluminosilicate zeolites having high silica to alumina ratios at temperatures of from about 350 to 600° C. and at pressures ranging between about 1 and 100 atmospheres.

It is also known in the art to convert methanol to light olefins using a silica-aluminum-phosphate catalyst, known as SAPO catalysts. It was considered that such catalysts had a higher selectivity to light olefins than the alumino-silicate zeolite catalysts employed in, for example, U.S. Pat. No. 4148835. For example, U.S. Pat. Nos. 4,861,938 , 5,126,308 and EP-A-0558839, all in the name of UOP, each disclose a process for the conversion of methanol into light olefins, in particular ethylene and propylene, using a silica-alumina-phosphate catalyst, in particular SAPO 34. These processes suffer from the problem that, in particular, when used in a fixed reactor, the selectivity to propylene of the catalyst is poor, and additionally too much ethylene is produced, leading to a relatively low propylene/ethylene molar ratio. This lowers the propylene purity in a fractionated cut containing $C_2$ and $C_3$ hydrocarbons. Also, as a result of the production of propane, the propylene purity in a $C_3$ cut maybe low. Furthermore, the propylene selectivity tends not to be stable over time. There is therefore a need to provide a conversion process which has a higher propylene selectivity than these known processes.

It is also known to crack catalytically an olefin-containing feedstock using a crystalline silicate catalyst, for example from WO-A-99/29802 (and its corresponding EP-A-0921176) and from WO-A-99/29805 (and its corresponding EP-A-0921181).

It is further known to use a crystalline silicate cracking catalyst to produce light olefins such as ethylene. For example, WO-A-98/56877 discloses a process for improving the conversion of a light hydrocarbon feedstock to light olefins comprising the steps of first contacting the hydrocarbon feedstock with a light olefin producing cracking catalyst, such as a ZSM-5 zeolite, and subsequently thermally cracking the unseparated stream to produce additional ethylene.

EP-A-0882692 discloses a process for the production of lower olefins with 2-3 C atoms which comprises reacting a methanol and/or dimethylether vapour and a reaction mixture containing water vapour in a first reactor on a first form selective catalyst at 280-570 degrees C. and 0.1-1 bar; withdrawing a product mixture containing 2-4 C olefin and 5C+ hydrocarbon from the first reactor; and cooling. The cooled first product mixture is fed through a separator and a second product mixture containing ethylene and propylene is withdrawn. A 5C+ stream is obtained, which is vaporised and mixed with water vapour. A ratio of H2O:hydrocarbons of 0.5-3:1 is used. The mixture containing water vapour is fed at 380-700 degrees C. to a second reactor containing a second form selective catalyst. A third product mixture is withdrawn from the second reactor which contains 50% olefinic components. This product mixture is cooled and fed to a separator. The catalyst in the first reactor may be a zeolite as disclosed in EP-B-0448000, a SAPO catalyst as disclosed in U.S. Pat. No. 4,524,235 and EP-A-0142156, or a silicalite catalyst as disclosed in U.S. Pat. No. 4,061,724. The catalyst in the second reactor may be a zeolite of the Pentasil-type having a silicon/aluminium atomic ratio of from 10:1 to 200: 1, variants of such catalysts being disclosed in EP-B-0369364, a SAPO catalyst or a silicalite catalyst.

It is an object of the present invention to provide a process for converting oxygen-containing hydrocarbon feedstocks which has a high yield of lighter olefins, and in particular propylene. It is another object of the invention to provide a process for producing propylene having a high propylene yield and purity.

It is a further object of the present invention to provide such a process which cam produce olefin effluents which are within, at least, a chemical grade quality.

It is yet a further object of the present invention to provide a process for producing olefins having a stable olefinic conversion and a stable product distribution over time.

The present invention provides a process for converting a hydrocarbon feedstock to provide an effluent containing light olefins, the process comprising passing a hydrocarbon feedstock, the feedstock containing at least one $C_1$ to $C_6$ aliphatic hetero compound selected from alcohols, ethers, carbonyl compounds and mixtures thereof and steam in an amount whereby the feedstock contains up to 80 weight % steam, through a reactor containing a crystalline silicate catalyst to produce an effluent including propylene, the crystalline silicate having been subjected to de-alumination by a steaming step and being selected from at least one of an MFI-type crystalline silicate having a silicon/aluminium atomic ratio of from 250 to 500 and an MEL-type crystalline silicate having a silicon/aluminium atomic ratio of from 150 to 800.

Preferably, the MFI-type crystalline silicate catalyst comprises silicalite.

Preferably, the at least one $C_1$ to $C_6$ aliphatic hetero compound is an oxygen containing compound.

Preferably, the hydrocarbon feedstock contains at least cone of methanol, ethanol, dimethyl ether, diethyl ether and mixtures thereof.

Preferably, the hydrocarbon feedstock is passed over the crystalline silicate at a reactor inlet temperature of from 350 to 650° C., more preferably from 450 to 550° C.

Preferably, the hydrocarbon feedstock is passed over the crystalline silicate at a WHSV of from 0.5 to 30 $h^{-1}$, the WHSV being based on the weight of the at least one $C_1$ to $C_6$ aliphatic hetero compound in the feedstock.

Preferably, the partial pressure of the at least one $C_1$ to $C_6$ aliphatic hetero compound in the feedstock when passed over the crystalline silicate is from 20 to 400 kPa.

The present invention further provides the use, in a process for converting a methanol feedstock in a reactor having a reactor inlet temperature of from 450 to 550° C. into an effluent containing propylene, of a crystalline silicate catalyst which has been de-aluminated by steaming thereby to have a silicon-aluminium atomic ratio of from 250 to 500 for increasing the propylene/ethylene ratio in the effluent.

The present invention yet further provides the use, in a process for converting a methanol feedstock in a reactor having a reactor inlet temperature of from 450 to 550° C. into an effluent containing propylene, of a crystalline silicate catalyst which has been de-aluminated by steaming thereby to have a silicon-aluminium atomic ratio of from 250 to 500 for increasing the propylene/propane ratio in the effluent.

The present invention still Her provides the use, in a process for converting a methanol feedstock in a reactor having a reactor inlet temperature of from 450 to 550° C. into an effluent containing propylene, of a crystalline silicate catalyst which has been de-aluminated by steaming thereby to have a silicon-aluminium atomic ratio of from 250 to 500, for enhancing the stability of the catalyst over time.

The present invention can thus provide a process wherein hydrocarbon streams (products) from refinery and petrochemical plants are selectively converted not only into light olefins, but particularly into propylene.

The hydrocarbon feedstock may be fed either undiluted or diluted with steam and/or an inert gas such as nitrogen. In the latter case, the absolute pressure of the feedstock constitutes the partial pressure of the hydrocarbon feedstock in the steam and/or the inert gas.

Figure 2:
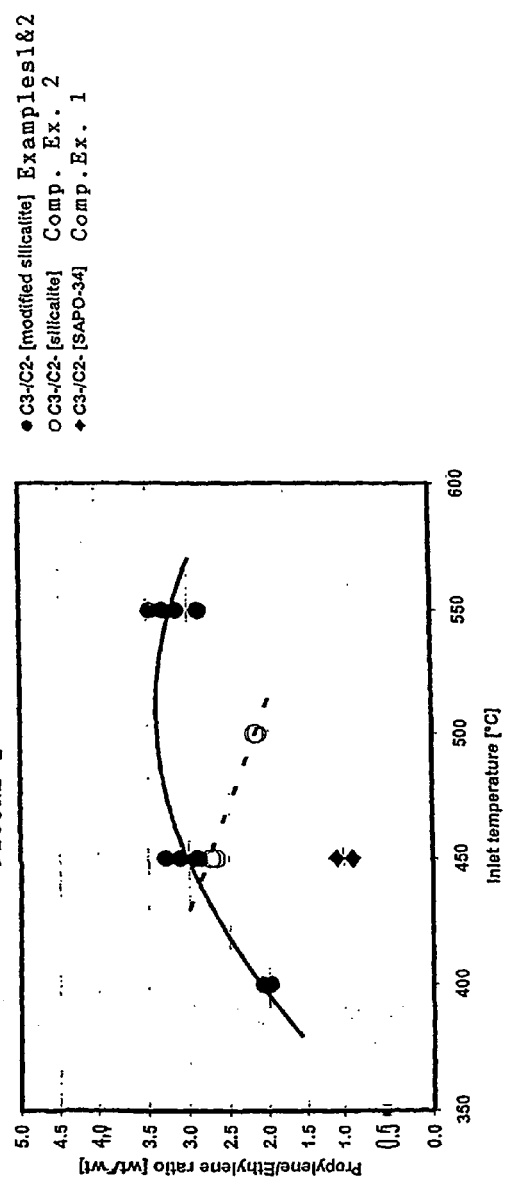

The various aspects of embodiments of the present invention will now be described in greater detail, by way of example only, with reference to the accompanying drawings, in which:

FIG. 1 shows the relationship between the yield, on a hydrocarbon basis, of various $C_2$ to $C_3$ hydrocarbon constituents in the effluent and inlet temperature in some Examples and Comparative Examples; and FIG. 2 shows the relationship between the propylene/ethylene ratio in the effluent and inlet temperature in some Examples and Comparative Examples.

In accordance with the present invention, catalytic conversion of a feedstock containing at least one $C_1$ to $C_6$ aliphatic hetero compound selected from alcohols, ethers, carbonyl compounds and mixture thereof, into an effluent containing light olefins, in particular ethylene and propylene, and selectively into propylene.

The $C_1$ to $C_6$ aliphatic alcohols may be monohydric and straight or branched and may be selected from methanol, ethanol, propanol and butanol. The ethers may be $C_2$ to $C_4$ ethers selected from dimethyl ether, diethyl ether or methyl ethyl ether. The carbonyl compounds maybe $C_2$ to $C_4$ carbonyl compounds selected from formaldehyde, dimethyl ketone, or acetic acid. The feedstock is most preferably selected from methanol, ethanol, dimethyl ether, diethyl ether and mixtures thereof, with methanol being particularly preferred.

In accordance with the process of the invention, the hydrocarbon feedstocks are selectively converted in the presence of an MFI-type or MEL-type catalyst so as to produce propylene in the resultant effluent. The catalyst and process conditions are selected whereby the process has a particular yield towards propylene in the effluent.

In accordance with a preferred aspect of the present invention, the catalyst comprises a crystalline silicate of the MFI family which may be a zeolite, a silicalite or any other silicate in that family or the MEL family which maybe a zeolite or any other silicate in that family. The three-letter designations "MFI" and "MEL" each represent a particular crystalline silicate structure type as established by the Structure Commission of the International Zeolite Association. Examples of MFI silicates are ZSM-5 and silicalite. An example of an MEL zeolite is ZSM-11 which is known in the art. Other examples are Boralite D, and silicalite-2 as described by the international Zeolite Association (Atlas of zeolite structure types, 1987, Butterworths).

The preferred crystalline silicates have pores or channels defined by ten oxygen rings and a high silicon/aluminium atomic ratio.

Crystalline silicates are microporous crystalline inorganic polymers based on a framework of $XO_4$ tetrahedra linked to each other by sharing of oxygen ions, where X maybe trivalent (e.g. Al, B, . . .) or tetravalent (e.g. Ge, Si, . . .). The crystal structure of a crystalline silicate is defined by the specific order in which a network of tetrahedral units are linked together. The size of the crystalline silicate pore openings is determined by the number off tetrahedral units, or, alternatively, oxygen atoms, required to form the pores and the nature of the cations that are present in the pores. They possess a unique combination of the following properties: high internal surface area; uniform pores with one or more discrete sizes; ion exchangeability, good thermal stability, and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bi-directional intersecting pore system with the following pore diameters: a straight channel along [010]: 0.53-0.56 nm and a sinusoidal channel along [100]:0.51-0.55 nm. Crystalline silicates with the MEL structure possess a bi-directional intersecting straight pore system with straight channels along [100] having pore diameters of 0.53-0.54 nm.

The crystalline silicate catalyst has structural and chemical properties and is employed under particular reaction conditions whereby the catalytic conversion to form light olefins, in particular propylene, readily proceeds.

The catalyst has a high silicon/aluminium atomic ratio, whereby the catalyst has relatively low acidity. In this specification, the term "silicon/aluminium atomic ratio" is intended to mean the Si/Al atomic ratio of the overall material, which may be determined by chemical analysis. In particular, for crystalline silicate materials, the stated Si/Al ratios apply not just to the Si/Al framework of the crystalline silicate but rather to the whole material.

Different reaction pathways can occur on the catalyst. Hydrogen transfer reactions are directly related to the strength and density of the acid sites on the catalyst, and such reactions are preferably suppressed by the use of high Si/Al ratios so as to avoid the formation of coke during the conversion process, thereby increasing the stability of the catalyst. Moreover, the use of high Si/Al atomic ratios has been found to increase the propylene selectivity of the catalyst, i.e. to reduce the amount of propane produced and/or to increase the propylene/ethylene ratio. This increases the purity of the resultant propylene.

In accordance with one aspect, a first type of MFI catalyst has a high silicon/aluminum atomic ratio of from 250 to 500, whereby the catalyst has relatively low acidity. Hydrogen transfer reactions are directly related to the strength and density of the acid sites on the catalyst, and such reactions are preferably suppressed so as to avoid the progressive formation of coke which in turn would otherwise decrease the stability of the catalyst over time. Such hydrogen transfer reactions tend to produce saturates such as paraffins, intermediate unstable dienes and cyclo-olefins, and aromatics, none of which favours conversion into light olefins. Cyclo-olefins are precursors of aromatics and coke-like molecules, especially in the presence of solid acids, i. e. an acidic solid catalyst. The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis.

With such high silicon/aluminum ratio in the crystalline silicate catalyst, a stable conversion of the hydrocarbon feedstock can be achieved, with a high propylene yield of from 20 to 90%, more preferably from 30 to 50%. The propylene selectivity is much that in the effluent the propylene/ethylene weight ratio is typically from 2 to 10 and/or the propylene/propane weight ratio is typically from $^{97}/_3$ to $^{99.9}/_{0.1}$. Such high silicon/aluminum ratios in the catalyst reduce the acidity of the catalyst, thereby also increasing the stability of the catalyst.

The MFI catalyst having a high silicon/aluminum atomic ratio for use in the catalytic conversion process of the present invention is manufactured by removing aluminum from a commercially available crystalline silicate. A typical commercially available silicalite has a silicon/aluminum atomic ratio of around 120. The commercially available MFI crystalline silicate is modified by a steaming process which reduces the tetrahedral aluminum in the crystalline silicate framework and converts the aluminum atoms into octahedral aluminum in the form of amorphous alumina. Although in the steaming step aluminum atoms are chemically removed from the crystalline silicate frameworks structure to form alumina particles, those particles cause partial obstruction of the pores or channels in the framework. This inhibits the conversion processes of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminum complex yields the overall effect of de-alumination of the MFI crystalline silicate. In this way by removing aluminum from the MFI crystalline silicate framework and then removing alumina formed therefrom from the pores, the process aims at achieving a substantially homogeneous de-alumination throughout the whole pore surfaces of the catalyst. This reduces the acidity of the catalyst, and thereby reduces the occurrence of hydrogen transfer reactions in the conversion process. The reduction of acidity ideally occurs substantially homogeneously throughout the pores defined in the crystalline silicate framework. This is because in the hydrocarbon conversion process hydrocarbon species can enter deeply into the pores. Accordingly, the reduction of acidity and thus the reduction ire hydrogen transfer reactions which would reduce the stability of the MFI catalyst are pursued throughout the whole pore structure in the framework. The Rework silicon/aluminum ratio is increased by this process to a value of from 250 to 500.

Instead of an MFI-type catalyst, the process of the invention may useean MEL-type crystalline silicate having a silicon/aluminium atomic ratio of from 150 to 800 which has been subjected to a steaming step. In accordance with this further aspect, an MEL catalyst for use in the catalytic hydrocarbon conversion process maybe manufactured by steaming an as-synthesised or commercially available crystalline silicate. The MEL crystalline silicate catalyst fop use in the invention most typically comprises a ZSM-11 catalyst which may be synthesised either using diaminooctane as the templating agent and sodium silicate as the silicon source or tetrabutyl phosphonium bromide as the templating agent and a silica sol as the silicon source. Thus the ZSM- 11 catalyst may be prepared by mixing sodium silicate with 1,8 diaminooctane together with aluminium sulphate to form a hydrogel which is then allowed to crystallise to form the crystalline silicate. The organic template material is then removed by calcining. Alternatively, the ZSM-11 catalyst is produced by reacting tetrabutyl phosphonium bromide and sodium hydroxide together with the silica sol prepared from colloidal silica. Again, a crystallisation is performed to produce the crystalline silicate and then the product is calcined.

In order to reduce the sodium content of the MEL crystalline silicate, the crystalline silicate is subjected to an ion exchange with a salt. Thereafter the material is dried. Typically, the crystalline silicate is subjected to ion exchange with ammonium ions, for example by immersing the crystalline silicate in an aqueous solution of $NH_4Cl$ or $NH_{NO3}$. Such an ion exchange step is desirable if the amount of sodium ions present in the crystalline silicate is so high that a crystalline sodium silicate phase is formed following calcination of die crystalline silicate which would be difficult to remove.

The initial MEL crystalline silicate is modified by a steaming process which, without being bound by theory, is believed to reduce the tetrahedral aluminium in the crystalline silicate framework and to convert the aluminium atoms into octahedral aluminium in the form of amorphous alumina. Although in the steaming step aluminium atoms are chemically removed from the MEL crystalline silicate framework structure to form alumina particles, those particles appear not to migrate and so do not cause partial obstruction of the pores or channels in the framework which would otherwise inhibit the conversion processes of the present invention. The steaming step has been found to improve significantly the propylene yield, propylene selectivity and catalyst stability in the catalytic conversion process.

The steam treatment on the MEL catalyst is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

Following the steaming step, the MEL catalyst is thereafter calcined, for example at a temperature of from 400 to 800° C. at atmospheric pressure for a period of from 1 to 10 hours.

Following the steaming step, the MEL catalyst may be contacted by a complexing agent for aluminium which may comprise an acid in an aqueous solution thereof or a salt of such an acid or a mixture of two or more such acids or salts. The complexing agent may in particular comprise an amine, such as ethyl diamine tetra acetic acid (EDTA) or a salt thereof, in particular the sodium salt thereof. Following the contacting of the MEL crystalline silicate by the complexing agent, the crystalline silicate may be subjected to a second ion exchange step for reducing the sodium content of the crystalline silicate still further, for example by contacting the catalyst with an ammonium nitrate solution.

The MEL or MFI crystalline silicate catalyst may be mixed with a binder, preferably an inorganic binder, and shaped to a desired shape, e-g. extruded pellets. The binder is selected so as to be resistant to the temperature and other conditions employed in the catalyst manufacturing process and in the subsequent catalytic conversion process. The binder is an inorganic material selected from clays, silica, metal oxides such as $ZrO_2$ and/or metals, or gels including mixtures of silica and metal oxides. The binder is preferably alumina-free. However, aluminium in certain chemical compounds as in $AlPO_4$'s may be used as the latter are quite inert and not acidic in nature. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of crystalline silicate and an inorganic oxide binder is referred to as a formulated crystalline silicate.

In mixing the catalyst with a binder, the catalyst maybe formulated into pellets, extruded into other shapes, or formed into a spray-dried powder.

Typically, the binder and the crystalline silicate catalyst are mixed together by an extrusion process. In such a process, the binder, for example silica, in the form of a gel is mixed with. the crystalline silicate catalyst material and the resultant mixture is extruded into the desired shape, for example pellets. Thereafter, the formulated crystalline silicate is calcined in air or an inert gas, typically at a temperature of from 200 to 900° C. for a period of from 1 to 48 hours.

The binder preferably does not contain any aluminium compounds, such as alumina. This is because as mentioned above the preferred catalyst has a selected silicon/aluminium ratio of the crystalline silicate. The presence of alumina in the binder yields other excess alumina if the binding step is performed prior to the aluminium extraction step. If the aluminium-containing binder is mixed with the crystalline silicate catalyst following aluminium extraction, this re-aluminates the catalyst. The presence of alumninium in the binder would tend to reduce the propylene selectivity of the catalyst, and to reduce the stability of the catalyst over time.

In addition, the Fixing of the catalyst with the binder may be carried out either before or after any steaming step.

The various preferred catalysts have been found to exhibit high stability, in particular being capable of giving a stable propylene yield over several days, e.g. up to ten days. This enables the catalytic conversion process to be performed continuously in two-parallel "swing" reactors wherein when one reactor is operating, the other reactor is undergoing catalyst regeneration. The catalyst also can be regenerated several times. The catalyst is also flexible in that it can be employed to crack a variety of feedstocks, either pure or mixtures, coming from different sources in the oil refinery or petrochemical plant and having different compositions.

In the catalytic conversion process, the process conditions are selected in order to provide high selectivity to-wards propylene, a stable conversion into propylene over time, and a stable product distribution in the effluent. Such objectives are favoured by the use of a low acid density in the catalyst (i.e. a high Si/Al atomic ratio) in conjunction with a low pressure, a high inlet temperature and a short contact time, all of which process parameters are interrelated and provide an overall cumulative effect (e.g. a higher pressure maybe offset or compensated by a yet higher inlet temperature). The process conditions are selected to disfavour hydrogen transfer reactions leading to the formation of paraffins, aromatics and coke precursors. The process operating conditions thus employ a high space velocity, a low pressure and a high reaction temperature.

The weight hourly space velocity(WHSV) with respect to the oxygen-containing hydrocarbon feedstock ranges from 0.5 to $30h^{-1}$, preferably from 1.0 to $20h^{-1}$. The oxygen-containing hydrocarbon feedstock is preferably fed at a total inlet pressure sufficient to convey the feedstock through the reactor. Preferably, the total absolute pressure in the reactor ranges from 0.5 to 10 bars. The oxygenated partial pressure ranges from 20 to 400 kPa, preferably from 50 to 200 kPa. A particularly preferred oxygenated partial pressure is 100 kPa. The oxygenates feedstocks may be fed undiluted or diluted with steam, e.g. from 0 to 80 wt % steam, typically about 30 wt % steam, and/or in an inert gas, e.g. nitrogen or hydrogen. The use of a low oxygenates partial pressure, for example atmospheric pressure, tends to lower the incidence of hydrogen transfer reactions in the conversion process, which in turn reduces the potential for coke formation which tends to reduce catalyst stability. Preferably, the inlet temperature of the feedstock ranges from 350 to 650° C., more preferably from 400 to 600° C., yet more preferably from 450 to 585° C., typically around 450° C. to 550° C.

The catalytic conversion process can be performed in a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" fixed bed reactors.

Since the catalyst exhibits high stability for an extended period, typically at least around ten days, the frequency of regeneration of the catalyst is low. More particularly, the catalyst may accordingly have a lifetime which exceeds one year.

The light fractions of the effluent, namely the $C_2$ and $C_3$ cuts, can contain more than 90% olefins (i.e. ethylene and propylene). Such cuts are sufficiently pure to constitute chemical grade olefin feedstocks. The propylene yield in such a process can range from 20 to 90%. The propylene/ethylene weight ratio typically ranges from 2 to 10, more typically from 2 to 5. The propylene/propane weight ratio typically ranges from 10 to 1000, more typically from 15 to 100. These two ratios maybe higher than obtainable using prior art processes described herein. The propylene/aromatics weight ratio may range from 2.5 to 100, more typically from 3to 10.

In accordance with the present invention therefore, hydrocarbon feedstocks containing at least one $C_1$ to $C_6$ aliphatic hetero compound selected from alcohols, ethers, carbonyl compounds and mixtures thereof are subject to a catalytic conversion process which selectively forms propylene as well as ethylene, and thereafter, the effluent is separated into a $C_2$ and $C_3$ combined product that is recovered in a common fractionation train, and into a $C_4$+product. The $C_2$ and $C_3$ combined product is high in propylene, and relatively low in ethylene and propane.

The present invention will now be described in greater detail with reference to the following non-limiting Examples.

EXAMPLE 1

In Example 1, a laboratory scale fixed bed reactor had provided therein a crystalline silicate catalyst of the MFI-type. The catalyst comprises silicalite which had a silicon/aluminium atomic ratio of 273 and had been produced by a de-alumnination process as described hereinabove.

More specifically, the silicalite catalyst was prepared by steaming 4.2 kg of silicalite at 550° C. for a period of 48 hours with steam in a rotating laboratory furnace. Thereafter, 2 kg of the steamed silicalite was then treated with an aqueous solution of the sodium salt of ethyl diamine tetraacetic acid (EDTA-Na$_2$), there being 8.4 liters of a 0.055 molar solution thereof for the 2 kg of silicalite. The treatment was for a period of 18 hours at boiling temperature. The silicalite was then subsequently filtered and washed thoroughly with de-ionised water. This process extracted aluminium from the silicalite.

Thereafter, an extruded catalyst was prepared using a kneader, in particular a Guittard type M5 No. 2295 kneader. In particular, 1640 g of the treated silicanlite, 112 g of silica powvder (DegussaFK500) and 726 of silicasol (Nyacol2040 from EKA containing about41% silica by weight) were mixed for a few minutes to homogonize them, and then 600 ml of distilled water was added to the mixture to obtain a paste, which was then mixed for another 30 minutes. After the 30 minute mixing time, 10 g of polyelectrolyte solution (Nalco 9779) were added to the mixture and kneaded for 1 minute. Then 30 g of metyl-hydroxy-ethyl-cellulose (Tylose from Hoechst MHB1000P2) were added. The loss on ignition. (LOI) was about 33 wt %. The extruder (Alexanderwerk type AGMR No. 04231162) was equipped with a die plate aperture of 2.5 mm, which was quadralobe shaped. The paste was passed 2 to 3 times through the extruder. The resultant extudates were air-dried over night, then dried at 110° C. for 16 hours in a drying oven with a heating rate of 60° C. per hour, and then calcined at a temperature of 600° C. for a period of 10 hours. Finally, the catalyst was subjected to ion-exchange, whereby 1740 g of the extruded catalyst was ion-exchanged using NH$_4$Cl (0.5 molar and 7310 ml of solution) twice, the first time being for a period of 18 hours and the second time being for a period of 3 hours, both at the boiling temperature of the solution. Finally, the catalyst was filtered off, -washed and calcined at a temperature of 400° C. for a period of 3 hours.

The resultant modified silicalite catalyst was in the form of particles of crushed extrudates of 35 to 45 mesh size. Chemical analysis of the catalyst indicate that the composition as $SiO_2$ 99.594 wt %, $Al_2O_3$ 0.310 wt %, $Na_2O$ 0.028 wt % and $Fe_2O_3$ 0.058 wt %. This provided a silicon/aluminium atomic ratio of 273.

The laboratory scale reactor had a diameter of 10 mm and was loaded with a catalyst load of 3 g. The reactor was subjected to a pre-treatment at 500° C. under nitrogen gas overnight. The reactor was operated at atmospheric pressure. The reactor was fed with an oxygenates feedstock comprising 70 wt % methanol and 30 wt % water, in the form of steam, at a methanol partial pressure of 56 kPa. The WHSV, with respect to the methanol, was 1.9 h$^{-1}$. The total time on stream [TOS] was 457 minutes. Initially, the reactor inlet temperature was 400° C. and after 270 minutes on stream, the reactor inlet temperature was increased to 450° C. The composition of the effluent is shown in Table 1. The composition of the effluent was analysed using an on-line apolar column DB-1, 0.4 micron, JNW Scientific Cat. No. 1271043).

It may be seen from Table 1 that the methanol was 100% converted throughout the time on stream. At a reactor inlet temperature of around 400° C., the propylene yield was around 22 wt % and the ethylene yield was around 11%. The propane yield was around 1.4 wt %. When the reactor temperature was increased to 450° C., the propylene yield was increased to around 30 wt % the ethylene yield decreased slightly to less than 10 wt %, and the propane yield decreased slightly as well. At 450° C., the propylene/ethylene weight ratio was about 3 or greater and the propylene/propane weight ratio was about 23 or greater. Accordingly, in this Example, the propylene selectivity was high, and the relatively high values of the propane/ethylene weight ratio and the propylene/propane weight ratio provided high propylene purity in a fractionated $C_2$ and $C_3$ combined cut.

The yields, on a hydrocarbon basis (water free), of propylene, ethylene and propane at the two temperatures in Example 1 are shown in FIG. 1. The propylene/ethylene weight ratios at the two temperatures in Example 1 are shown in FIG. 2.

EXAMPLE 2

In Example 2 the process of Example 1 was repeated with the same feedstock, catalyst and WHSV but at a higher reactor inlet temperature of 550° C. The results are shown in Table 2.

The Example was carried out for a total of 185 minutes on stream at a temperature of 550° C.

It may be seen that the propylene yield is increased at the higher temperature of 550° C. as compared to the temperatures of Example 1. The propylene yield was about 40 wt % after 185 minutes on stream. At that time, the propylene/ethylene weight ratio was about 3.3 and the propylene/propane weight ratio was about 38. Again, this indicates not only high propylene selectivity, but high propylene purity in a fractionated $C_2$ and $C_3$ combined cut. Like Example 2, Example 1 shows high stability of the catalyst when used in a fixed bed reactor over time.

The yields, on a hydrocarbon basis (water free), of propylene, ethylene and propane at the temperature in Example 2 are shown in FIG. 1. The propylene/ethylene weight ratios at the temperature in Example 2 are shown in FIG. 2

COMPARATIVE EXAMPLE 1

In this Comparative Example, Example 1 was repeated using a different catalyst, namely a silica-alumina-phosphate catalyst, in particular SAPO 34 available from UOP of Des Plaines, Ill., USA, having a particle size of 35-45 mesh. The same feedstock and WHSV were employed as in Examples 1 and 2. The reactor temperature was a constant 450° C. A maximum time on stream was 211 minutes. The results are shown in Table 3.

As may be seen from Table 3, initially the propylene yield was higher than the ethylene yield but the propylene/ethylene weight ratio rapidly decreased below unity. Therefore the propylene selectivity of this catalyst is lower than that employed in the present invention. Moreover, after only 149 minutes on stream the methanol conversion fell below 100% and the effluent included the methanol from the feedstock as well as dimethyl ether. This shows that the SAPO 34 catalyst when used in a fixed bed had a low stability.

The propylene/ethylene weight ratios for the catalyst of Comparative Example 1 are shown in FIG. 2.

COMPARATIVE EXAMPLE 2

In this Comparative Example, Comparative Example 1 was repeated using a different catalyst, the catalyst being a silicalite available in commerce under product number S-115 Na-6 from UOP of Des Plaines, Ill., USA, the silicalite having a silicon/aluminium atomic ratio of 177. The silicalite had a chemical composition of $SiO_2$ 99.450 wt %, $Al_2O_3$ 0.478 wt %, $Na_2O$ 0.006 wt % and $Fe_2O_3$ 0.052 wt %, yielding a silicon/aluminium ratio of 177. The silicalite was in the form of particles of 35 to 45 mesh. The WHSV was $1.9h^{-1}$ as in Examples 1 and 2 and in Comparative Example 1 and the feed also comprised 70 wt % methanol and 30 wt % steam. The process of Comparative Example 2 was carried out at two reactor inlet temperatures, namely at a temperature of 450° C. for up to 208 minutes on stream, and at a temperature of 500° C. thereafter up to a total time on stream of 380 minutes. The results are summarised in Table 4.

From Table 4, it may be seen that while the stability of the catalyst is higher as compared to Comparative Example 1, the propylene selectivity and purity are less than obtained in accordance with Examples 1 and 2. Thus at the same comparison temperature of 450° C., in Comparative Example 2 the propylene yield was consistently less than 30 wt %, lower than that achievable in Example 1 at the corresponding temperature. Moreover, at that temperature of 450° C., the propylene/ethylene weight ratio was about 2.7, lower than obtainable in Example 1. Furthermore, in Comparative Example 2, the propylene/propane weight ratio aLt a reactor inlet temperature of 450° C. was about 9 or less, thereby indicating lower propylene purity corresponding to that obtainable using the corresponding temperature in Example 1. In Comparative Example 2 in yet a higher reactor inlet temperature of 500° C., the ethylene yield and the propane yield were higher than that obtainable in Example 1 of 450° C.

The yields, on a hydrocarbon basis (water free), of propylene, ethylene and propane at the two temperatures in Comparative Example 2 are shown in FIG. 1. The propylene/ethylene weight ratios at the two temperatures in Comparative Example 2 are shown in FIG. 2.

COMPARATIVE EXAMPLE 3

In this Comparative Example, Comparative Example 1 was repeated but using a feed comprising 100 wt % methanol. The same WHSV aid reactor temperature were employed as in Comparative Example 1. The maximum time on stream was 102 minutes. The results are shown in Table 5.

Table 5 shows that for Comparative Example 3, although the propylene yield is more stabilised compared to Comparative Example 1, the propylene/ethylene ratio rapidly decreased below unity, and therefore is lower than that achievable using Examples 1 and 2.

TABLE 1

| | Example 1 | | | | |
|---|---|---|---|---|---|
| | TOS [min] | | | | |
| | 145 | 270 | 332 | 395 | 457 |
| Temperature [° C.] | 400 | 400 | 450 | 450 | 450 |
| Conversion [%] | 100 | 100 | 100 | 100 | 100 |
| Yields [wt %] | | | | | |
| C1 | 1.44 | 1.11 | 4.76 | 2.96 | 3.30 |
| C2− | 11.20 | 10.96 | 10.19 | 9.88 | 9.44 |
| C2 | 0.12 | 0.12 | 0.14 | 0.13 | 0.11 |
| C3− | 22.06 | 22.52 | 29.25 | 30.61 | 30.95 |
| C3 | 1.49 | 1.38 | 1.51 | 1.30 | 1.34 |
| C4's | 4.71 | 4.19 | 3.05 | 2.65 | 2.76 |
| C4−'s | 19.06 | 16.05 | 18.80 | 18.85 | 19.24 |
| C5+'s | 39.92 | 43.66 | 32.30 | 33.62 | 32.85 |
| Total | 100.00 | 100.00 | 100.00 | 100.00 | 100.00 |
| Aromatics | | | | | |
| C6 | 0.49 | 0.49 | 0.81 | 0.82 | 0.79 |
| C7 | 0.99 | 0.90 | 1.32 | 1.36 | 1.11 |
| C8 | 6.13 | 5.69 | 5.61 | 6.03 | 5.12 |
| Total aromatics | 7.61 | 7.08 | 7.74 | 8.21 | 7.03 |

TABLE 2

| | Example 2 | | |
|---|---|---|---|
| | TOS [min] | | |
| | 61 | 123 | 185 |
| Temperature [° C.] | 550 | 550 | 550 |
| Conversion [%] | 100 | 100 | 100 |
| Yields [wt %] | | | |
| C1 | 7.78 | 4.99 | 4.68 |
| C2− | 12.68 | 12.69 | 12.30 |
| C2 | 0.30 | 0.31 | 0.30 |
| C3− | 36.25 | 39.81 | 40.50 |
| C3 | 0.95 | 1.08 | 1.07 |
| C4's | 0.90 | 0.74 | 0.69 |
| C4−'s | 13.60 | 15.56 | 16.12 |
| C5+'s | 27.55 | 24.83 | 24.34 |
| Total | 100.00 | 100.00 | 100.00 |
| Aromatics | | | |
| C6 | 0.44 | 0.51 | 0.54 |
| C7 | 3.47 | 3.45 | 3.20 |
| C8 | 7.59 | 6.87 | 6.96 |
| Total aromatics | 11.50 | 10.84 | 10.70 |

TABLE 3

Comparative Example 1

| | TOS [min] | | | |
|---|---|---|---|---|
| | 24 | 86 | 149 | 211 |
| Temperature [° C.] | 450 | 450 | 450 | 450 |
| Conversion [%] | 100 | 100 | 93.6 | 78.6 |
| Yields [wt %] | | | | |
| C1 | 2.09 | 4.29 | 5.22 | 0 |
| C2− | 32.83 | 42.86 | 33.02 | 0 |
| C2 | 0.78 | 0.86 | 0.69 | 0 |
| C3− | 35.78 | 37.21 | 27.84 | 0 |
| C3 | 3.26 | 0.97 | 0.57 | 0 |
| DME | 0 | 0 | 15.38 | 77.92 |
| Methanol | 0 | 0 | 6.37 | 21.36 |
| C4's | 0.43 | 0.08 | 0.13 | 0 |
| C4−'s | 15.93 | 10.11 | 7.35 | 0.72 |
| C5+'s | 8.84 | 3.55 | 2.28 | 0 |
| Total | 99.95 | 99.93 | 98.84 | 100.00 |

TABLE 4

Comparative Example 2

| | TOS [min] | | | | | |
|---|---|---|---|---|---|---|
| | 20 | 137 | 199 | 208 | 324 | 386 |
| Temperature [° C.] | 450 | 450 | 450 | 450 | 500 | 500 |
| Conversion [%] | 100 | 100 | 100 | 100 | 100 | 100 |
| Yields [wt %] | | | | | | |
| C1 | 3.03 | 2.29 | 1.69 | 1.77 | 4.40 | 4.33 |
| C2− | 9.71 | 9.63 | 9.58 | 10.21 | 14.27 | 14.59 |
| C2 | 0.30 | 0.32 | 0.32 | 0.32 | 0.60 | 0.63 |
| C3− | 28.14 | 25.66 | 26.02 | 27.87 | 30.89 | 31.09 |
| C3 | 3.13 | 3.70 | 3.42 | 3.07 | 2.95 | 2.98 |
| C4's | 4.48 | 5.50 | 4.96 | 4.16 | 2.39 | 2.35 |
| C4−'s | 21.86 | 21.22 | 21.18 | 21.48 | 18.10 | 17.67 |
| C5+'s | 29.31 | 31.61 | 32.80 | 31.06 | 26.33 | 26.30 |
| Total | 100.0 | 100.0 | 100.0 | 100.0 | 99.9 | 99.9 |
| Aromatics | | | | | | |
| C6 | 2.12 | 2.29 | 2.36 | 2.95 | 1.11 | 1.06 |
| C7 | 2.44 | 2.51 | 3.02 | 2.86 | 4.26 | 4.39 |
| C8 | 5.82 | 5.82 | 6.73 | 7.38 | 9.15 | 9.52 |
| Total aromatics | 10.38 | 10.62 | 12.12 | 13.20 | 14.52 | 14.98 |

TABLE 5

Comparative Example 3

| | TOS [min] | | |
|---|---|---|---|
| | 20 | 61 | 102 |
| Temperature [° C.] | 450 | 450 | 450 |
| Conversion [%] | 100 | 100 | 100 |
| Yields [wt %] | | | |
| C1 | 13.09 | 8.19 | 8.73 |
| C2− | 30.12 | 41.33 | 42.64 |
| C2 | 0.56 | 0.74 | 0.77 |
| C3− | 33.03 | 34.69 | 34.76 |
| C3 | 2.36 | 1.15 | 0.78 |
| DME | 0.00 | 0.00 | 0.00 |
| Methanol | 0.00 | 0.00 | 0.00 |
| C4's | 0.37 | 0.10 | 0.06 |
| C4−'s | 13.59 | 10.20 | 8.91 |
| C5+'s | 6.81 | 3.54 | 3.20 |
| Total | 99.93 | 99.93 | 99.85 |
| C3−/C2− | 1.10 | 0.84 | 0.82 |

The invention claimed is:

1. A process for converting a carbon containing feedstock to provide an effluent containing light olefins, the process comprising:
   forming a catalyst, wherein the catalyst is formed by
      supplying an MEL crystalline silicate catalyst;
      steam treating the MEL crystalline silicate catalyst;
      after steam treating, contacting the MEL crystalline silicate catalyst with a complexing agent for aluminum;
      after contact with the complexing agent, reducing the sodium content of the MEL crystalline silicate catalyst by subjecting the MEL crystalline silicate catalyst to ion exchange with a salt;
      calcining the MEL crystalline silicate catalyst after reducing the sodium content of the MEL crystalline silicate catalyst;
   passing a feedstock containing carbon containing compounds consisting essentially of $C_1$ to $C_6$ aliphatic hetero compounds selected from the group consisting of alcohols, ethers, carbonyl compounds and mixtures thereof and containing steam in an amount up to 80 weight % of said feedstock, through a reactor containing the catalyst to produce an effluent including propylene which is recovered from the reactor, wherein the feedstock is passed over the crystalline silicate at a reactor inlet temperature of about 550° C.

2. A process according to claim 1 wherein the carbon containing feedstock contains at least one hetero compound selected from the group consisting of methanol, ethanol, dimethyl ether, diethyl ether and mixtures thereof.

3. A process according to claim 1 wherein the carbon containing feedstock is passed over the crystalline silicate at a WHSV of from 0.5 to 30 $h^{-1}$, the WHSV being based on the weight of the at least one $C_1$ to $C_6$ aliphatic hetero compound in the feedstock.

4. A process according to claim 3 wherein the partial pressure of the at least on $C_1$ to $C_6$ aliphatic hetero compound in the feedstock when passed over the crystalline silicate is from 20 to 400 kPa.

5. The process of claim 1 wherein said feedstock comprises methanol and said reactor is operated under conversion conditions comprising an inlet temperature within the range of 450-550° C.

6. The process of claim 5 wherein said reactor is operated under conversion conditions providing a product containing propylene and ethylene and having a propylene/ethylene ratio which is greater than the propylene/ethylene ratio of a conversion product produced by the conversion of a methanol-containing feedstock operated at an inlet temperature in said reactor of 400° C.

7. The process of claim 5 wherein said reactor is operated under conversion conditions providing a product containing propylene and propane and having a propylene/propane ratio which is greater than the propylene/propane ratio of a conversion product produced by the conversion of a methanol-containing feedstock operated at an inlet temperature of 400° C.

8. The process of claim 1, wherein the effluent comprises a propylene/ethylene weight ratio ranging from 2 to 10.

9. The process of claim 1, wherein the effluent comprises a propylene/ethylene weight ratio ranging from 2 to 5.

10. The process of claim 1, wherein the salt comprises ammonium ions.

11. The process of claim 1, wherein the complexing agent comprises an acid in an aqueous solution, a salt of the acid in aqueous solution, or combinations thereof.

12. The process of claim 1, wherein the propylene yield is above 35wt %.

13. The process of claim 12, wherein the time on stream is about 61 minutes.

14. The process of claim 12, wherein the time on stream is about 123 minutes.

15. The process of claim 12, wherein the time on stream is about 185 minutes.

* * * * *